US009076427B2

(12) United States Patent
Alderson et al.

(10) Patent No.: US 9,076,427 B2
(45) Date of Patent: Jul. 7, 2015

(54) ERROR-SIGNAL CONTENT CONTROLLED ADAPTATION OF SECONDARY AND LEAKAGE PATH MODELS IN NOISE-CANCELING PERSONAL AUDIO DEVICES

(71) Applicant: Cirrus Logic, Inc., Austin, TX (US)

(72) Inventors: Jeffrey Alderson, Austin, TX (US); Jon D. Hendrix, Wimberly, TX (US); Yang Lu, Austin, TX (US)

(73) Assignee: Cirrus Logic, Inc., Austin, TX (US)

( * ) Notice: Subject to any disclaimer, the term of this patent is extended or adjusted under 35 U.S.C. 154(b) by 307 days.

(21) Appl. No.: 13/787,906

(22) Filed: Mar. 7, 2013

(65) Prior Publication Data

US 2013/0301849 A1 Nov. 14, 2013

Related U.S. Application Data

(60) Provisional application No. 61/645,265, filed on May 10, 2012.

(51) Int. Cl.
*A61F 11/06* (2006.01)
*G10K 11/16* (2006.01)
*G10K 11/178* (2006.01)

(52) U.S. Cl.
CPC ............ *G10K 11/16* (2013.01); *G10K 11/1784* (2013.01); *G10K 2210/108* (2013.01); *G10K 2210/3023* (2013.01);
(Continued)

(58) Field of Classification Search
USPC .............................................. 381/71.11, 71.6
See application file for complete search history.

(56) References Cited

U.S. PATENT DOCUMENTS 5,251,263 A 10/1993 Andrea et al.
5,278,913 A 1/1994 Delfosse et al.
5,337,365 A 8/1994 Hamabe et al.
(Continued)

FOREIGN PATENT DOCUMENTS

DE 102011013343 A1 9/2012
EP 1880699 A2 1/2008
(Continued)

OTHER PUBLICATIONS

U.S. Appl. No. 14/029,159, filed Sep. 17, 2013, Li, et al.
(Continued)

*Primary Examiner* — Quynh Nguyen
(74) *Attorney, Agent, or Firm* — Mitch Harris, Atty at Law, LLC; Andrew M. Harris

(57) ABSTRACT

A personal audio device, such as a wireless telephone, generates an anti-noise signal from a microphone signal and injects the anti-noise signal into the speaker or other transducer output to cause cancellation of ambient audio sounds. The microphone measures the ambient environment, but also contains a component due to the transducer acoustic output. An adaptive filter is used to estimate the electro-acoustical path from the noise-canceling circuit through the transducer to the at least one microphone so that source audio can be removed from the microphone signal. A determination of the relative amount of the ambient sounds present in the microphone signal versus the amount of the transducer output of the source audio present in the microphone signal is made to determine whether to update the adaptive response.

36 Claims, 4 Drawing Sheets

(52) U.S. Cl.
CPC . *G10K 2210/503* (2013.01); *G10K 2210/3055* (2013.01); *G10K 2210/505* (2013.01); *G10K 2210/506* (2013.01)

(56) References Cited

U.S. PATENT DOCUMENTS 5,410,605 A 4/1995 Sawada et al.
5,425,105 A 6/1995 Lo et al.
5,586,190 A 12/1996 Trantow et al.
5,640,450 A 6/1997 Watanabe
5,699,437 A 12/1997 Finn
5,706,344 A 1/1998 Finn
5,768,124 A 6/1998 Stothers et al.
5,815,582 A 9/1998 Claybaugh et al.
5,946,391 A 8/1999 Dragwidge et al.
5,991,418 A 11/1999 Kuo
6,041,126 A 3/2000 Terai et al.
6,118,878 A 9/2000 Jones
6,219,427 B1 4/2001 Kates et al.
6,418,228 B1 7/2002 Terai et al.
6,434,246 B1 8/2002 Kates et al.
6,434,247 B1 8/2002 Kates et al.
6,768,795 B2 7/2004 Feltstrom et al.
6,850,617 B1 2/2005 Weigand
7,058,463 B1 6/2006 Ruha et al.
7,103,188 B1 9/2006 Jones
7,181,030 B2 2/2007 Rasmussen et al.
7,330,739 B2 2/2008 Somayajula
7,365,669 B1 4/2008 Melanson
7,742,790 B2 6/2010 Konchitsky et al.
8,019,050 B2 9/2011 Mactavish et al.
8,249,262 B2 8/2012 Chua et al.
8,290,537 B2 10/2012 Lee et al.
8,379,884 B2 2/2013 Horibe et al.
8,401,200 B2 3/2013 Tiscareno et al.
2001/0053228 A1 12/2001 Jones
2002/0003887 A1 1/2002 Zhang et al.
2004/0165736 A1 8/2004 Hetherington et al.
2004/0167777 A1 8/2004 Hetherington et al.
2004/0264706 A1 12/2004 Ray et al.
2005/0117754 A1 6/2005 Sakawaki
2005/0240401 A1 10/2005 Ebenezer
2006/0153400 A1 7/2006 Fujita et al.
2007/0030989 A1 2/2007 Kates
2007/0033029 A1 2/2007 Sakawaki
2007/0038441 A1 2/2007 Inoue et al.
2007/0053524 A1 3/2007 Haulick et al.
2007/0076896 A1 4/2007 Hosaka et al.
2007/0154031 A1 7/2007 Avendano et al.
2007/0258597 A1 11/2007 Rasmussen et al.
2007/0297620 A1 12/2007 Choy
2008/0019548 A1 1/2008 Avendano
2008/0181422 A1 7/2008 Christoph
2008/0226098 A1 9/2008 Haulick et al.
2009/0012783 A1 1/2009 Klein
2009/0034748 A1 2/2009 Sibbald
2009/0041260 A1 2/2009 Jorgensen et al.
2009/0046867 A1 2/2009 Clemow
2009/0196429 A1 8/2009 Ramakrishnan et al.
2009/0220107 A1 9/2009 Every et al.
2009/0238369 A1 9/2009 Ramakrishnan et al.
2009/0245529 A1 10/2009 Asada et al.
2009/0254340 A1 10/2009 Sun et al.
2009/0290718 A1 11/2009 Kahn et al.
2009/0296965 A1 12/2009 Kojima
2009/0304200 A1 12/2009 Kim et al.
2010/0014683 A1 1/2010 Maeda et al.
2010/0014685 A1 1/2010 Wurm
2010/0061564 A1 3/2010 Clemow et al.
2010/0069114 A1 3/2010 Lee et al.
2010/0082339 A1 4/2010 Konchitsky et al.
2010/0098263 A1 4/2010 Pan et al.
2010/0124335 A1 5/2010 Stothers et al.
2010/0124336 A1 5/2010 Shridhar et al.
2010/0166203 A1 7/2010 Peissig et al.
2010/0195838 A1 8/2010 Bright
2010/0195844 A1 8/2010 Christoph et al.
2010/0272276 A1 10/2010 Carreras et al.
2010/0272283 A1 10/2010 Carreras et al.
2010/0274564 A1 10/2010 Bakalos et al.
2010/0296666 A1 11/2010 Lin
2010/0296668 A1 11/2010 Lee et al.
2010/0310086 A1 12/2010 Magrath et al.
2010/0322430 A1 12/2010 Isberg
2011/0007907 A1 1/2011 Park et al.
2011/0106533 A1 5/2011 Yu
2011/0142247 A1 6/2011 Fellers et al.
2011/0144984 A1 6/2011 Konchitsky
2011/0158419 A1 6/2011 Theverapperuma et al.
2011/0222698 A1 9/2011 Asao et al.
2011/0249826 A1 10/2011 Van Leest
2011/0288860 A1 11/2011 Schevciw et al.
2011/0293103 A1 12/2011 Park et al.
2011/0299695 A1 12/2011 Nicholson
2011/0317848 A1 12/2011 Ivanov et al.
2012/0135787 A1 5/2012 Kusunoki et al.
2012/0140943 A1 6/2012 Hendrix et al.
2012/0170766 A1 7/2012 Alves et al.
2012/0207317 A1 8/2012 Abdollahzadeh Milani et al.
2012/0250873 A1 10/2012 Bakalos et al.
2012/0259626 A1 10/2012 Li et al.
2012/0300958 A1 11/2012 Klemmensen
2012/0308021 A1 12/2012 Kwatra et al.
2012/0308024 A1 12/2012 Alderson et al.
2012/0308025 A1 12/2012 Hendrix et al.
2012/0308026 A1 12/2012 Kamath et al.
2012/0308027 A1 12/2012 Kwatra
2012/0308028 A1 12/2012 Kwatra et al.
2012/0310640 A1 12/2012 Kwatra et al.
2013/0010982 A1 1/2013 Elko et al.
2013/0243225 A1 9/2013 Yokota
2013/0272539 A1 10/2013 Kim et al.
2013/0287218 A1 10/2013 Alderson et al.
2013/0287219 A1 10/2013 Hendrix et al.
2013/0301842 A1 11/2013 Hendrix et al.
2013/0301846 A1 11/2013 Alderson et al.
2013/0301847 A1 11/2013 Alderson et al.
2013/0301848 A1 11/2013 Zhou et al.
2013/0343556 A1 12/2013 Bright
2013/0343571 A1 12/2013 Rayala et al.
2014/0044275 A1 2/2014 Goldstein et al.
2014/0050332 A1 2/2014 Nielsen et al.
2014/0086425 A1 3/2014 Jensen et al.
2014/0177851 A1 6/2014 Kitazawa et al.
2014/0211953 A1 7/2014 Alderson et al.
2014/0270222 A1 9/2014 Hendrix et al.
2014/0270223 A1 9/2014 Li et al.
2014/0270224 A1 9/2014 Zhou et al.

FOREIGN PATENT DOCUMENTS

EP 1947642 A1 7/2008
EP 2133866 A1 12/2009
EP 2216774 A1 8/2010
EP 2395500 A1 12/2011
EP 2395501 A1 12/2011
GB 2401744 A 11/2004
GB 2455821 A 6/2009
GB 2455824 A 6/2009
GB 2455828 A 6/2009
GB 2484722 A 4/2012
JP H06-186985 A 7/1994
WO WO 03/015074 A1 2/2003
WO WO 2004009007 A1 1/2004
WO WO 2007007916 A1 1/2007
WO WO 2007113487 A1 11/2007
WO WO 2010117714 A1 10/2010
WO WO 2012134874 A1 10/2012

OTHER PUBLICATIONS

U.S. Appl. No. 14/062,951, filed Oct. 25, 2013, Zhou, et al.
Black, John W., "An Application of Side-Tone in Subjective Tests of Microphones and Headsets", Project Report No. NM 001 064.01.20,

(56) References Cited

OTHER PUBLICATIONS

Research Report of the U.S. Naval School of Aviation Medicine, Feb. 1, 1954, 12 pages (pp. 1-12 in pdf), Pensacola, FL, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.
U.S. Appl. No. 14/197,814, filed Mar. 5, 2014, Kaller, et al.
U.S. Appl. No. 14/210,537, filed Mar. 14, 2014, Abdollahzadeh Milani, et al.
U.S. Appl. No. 14/210,589, filed Mar. 14, 2014, Abdollahzadeh Milani, et al.
Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.
Therrien, et al., "Sensory Attenuation of Self-Produced Feedback: The Lombard Effect Revisited", PLOS One, Nov. 2012, pp. 1-7, vol. 7, Issue 11, e49370, Ontario, Canada.
U.S. Appl. No. 13/686,353, filed Nov. 27, 2012, Hendrix, et al.
U.S. Appl. No. 13/795,160, filed Mar. 12, 2013, Hendrix, et al.
U.S. Appl. No. 13/692,367, filed Dec. 3, 2012, Alderson, et al.
U.S. Appl. No. 13/722,119, filed Dec. 20, 2012, Hendrix, et al.
U.S. Appl. No. 13/727,718, filed Dec. 27, 2012, Alderson, et al.
U.S. Appl. No. 13/784,018, filed Mar. 4, 2013, Alderson, et al.
U.S. Appl. No. 13/729,141, filed Dec. 28, 2012, Zhou, et al.
U.S. Appl. No. 13/794,931, filed Mar. 12, 2013, Lu, et al.
U.S. Appl. No. 13/794,979, filed Mar. 12, 2013, Alderson, et al.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.
Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.
Jin, et al. "A simultaneous equation method-based online secondary path modeling algorithm for active noise control", Journal of Sound and Vibration, Apr. 25, 2007, pp. 455-474, vol. 303, No. 3-5, London, GB.
Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.
Rao, et al., "A Novel Two State Single Channel Speech Enhancement Technique", India Conference (INDICON) 2011 Annual IEEE, IEEE, Dec. 2001, 6 pages (pp. 1-6 in pdf), Piscataway, NJ, US.
Rangachari, et al., "A noise-estimation algorithm for highly non-stationary environments", Speech Communication, Feb. 2006, pp. 220-231, vol. 48, No. 2. Elsevier Science Publishers.
U.S. Appl. No. 13/968,007, filed Aug. 15, 2013, Hendrix, et al.
Parkins, et al., "Narrowband and broadband active control in an enclosure using the acoustic energy density", J. Acoust. Soc. Am. Jul. 2000, pp. 192-203, vol. 108, issue 1, US.
Feng, et al.., "A broadband self-tuning active noise equaliser", Signal Processing, Oct. 1, 1997, pp. 251-256, vol. 62, No. 2, Elsevier Science Publishers B.V. Amsterdam, NL.
Zhang, et al., "A Robust Online Secondary Path Modeling Method with Auxiliary Noise Power Scheduling Strategy and Norm Constraint Manipulation", IEEE Transactions on Speech and Audio Processing, IEEE Service Center, Jan. 1, 2003, pp. 45-53, vol. 11, No. 1, NY.
Lopez-Gaudana, et al., "A hybrid active noise cancelling with secondary path modeling", 51st Midwest Symposium on Circuits and Systems, MWSCAS 2008, Aug. 10-13, 2008, pp. 277-280, IEEE, Knoxville, TN.
International Search Report and Written Opinion in PCT/US2013/037051, mailed on Feb. 13, 2014, 11 pages (pp. 1-11 in pdf).
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2012, Lu, et al.
U.S. Appl. No. 13/724,656, filed Dec. 21, 2012, Lu, et al.
U.S. Appl. No. 14/252,235, filed Apr. 14, 2014, Lu, et al.
U.S. Appl. No. 13/968,013, filed Aug. 15, 2013, Abdollahzadeh Milani, et al.
U.S. Appl. No. 13/924,935, filed Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson et al.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.

(56) References Cited

OTHER PUBLICATIONS

Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Caudana, Edgar Omar, "Active Noise Cancellation: The Unwanted Signal and The Hybrid Solution", Adaptive Filtering Applications, Dr. Lino Garcia (Ed.), Jul. 2011, pp. 49-84, ISBN: 978-953-307-306-4, InTech.
Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.
Hurst, et al., "An improved double sampling scheme for switched-capacitor delta-sigma modulators", 1992 IEEE Int. Symp. On Circuits and Systems, May 10-13, 1992, vol. 3, pp. 1179-1182, San Diego, CA.

ERROR-SIGNAL CONTENT CONTROLLED ADAPTATION OF SECONDARY AND LEAKAGE PATH MODELS IN NOISE-CANCELING PERSONAL AUDIO DEVICES

This U.S. Patent Application Claims priority under 35 U.S.C. §119(e) to U.S. Provisional Patent Application Ser. No. 61/645,265 filed on May 10, 2012.

BACKGROUND OF THE INVENTION

1. Field of the Invention

The present invention relates generally to personal audio devices such as wireless telephones that include adaptive noise cancellation (ANC), and more specifically, to control of ANC in a personal audio device that uses a measure of error signal content to control adaptation of secondary and leakage path estimates.

2. Background of the Invention

Wireless telephones, such as mobile/cellular telephones, cordless telephones, and other consumer audio devices, such as MP3 players, are in widespread use. Performance of such devices with respect to intelligibility can be improved by providing noise-canceling using a microphone to measure ambient acoustic events and then using signal processing to insert an anti-noise signal into the output of the device to cancel the ambient acoustic events.

Noise-canceling operation can be improved by measuring the transducer output of a device to determine the effectiveness of the noise-canceling using an error microphone. The measured output of the transducer is ideally the source audio, e.g., downlink audio in a telephone and/or playback audio in either a dedicated audio player or a telephone, since the noise-canceling signal(s) are ideally canceled by the ambient noise at the location of the transducer. To remove the source audio from the error microphone signal, the secondary path from the transducer through the error microphone can be estimated and used to filter the source audio to the correct phase and amplitude for subtraction from the error microphone signal. Similarly, ANC performance can be improved by modeling the leakage path from the transducer to the reference microphone. However, when source audio is absent, the secondary path estimate and leakage path estimate cannot typically be updated. Further, when source audio is low in amplitude, the secondary path estimate and leakage path estimate may not be accurately updated, as the error microphone signal and/or the reference microphone signal may be dominated by other sounds.

Therefore, it would be desirable to provide a personal audio device, including wireless telephones, that provides noise cancellation using a secondary path estimate and/or leakage path estimates to remove the output of the transducer from error and reference signals, respectively, and that can determine whether or not to adapt the secondary path and leakage path estimates.

SUMMARY OF THE INVENTION

The above-stated objective of providing a personal audio device providing noise-cancelling including a secondary path and/or leakage path estimate that are adapted when sufficient source audio magnitude relative to ambient sounds is detected, is accomplished in a personal audio device, a method of operation, and an integrated circuit.

The personal audio device includes an output transducer for reproducing an audio signal that includes both source audio for providing to a listener and an anti-noise signal for countering the effects of ambient audio sounds in an acoustic output of the transducer. A microphone provides a measurement of ambient sounds, but that contains a component of source audio due to the transducer output. The personal audio device further includes an adaptive noise-canceling (ANC) processing circuit within the housing for adaptively generating an anti-noise signal from the at least one microphone signal such that the anti-noise signal causes substantial cancellation of the ambient audio sounds. The ANC processing circuit controls adaptation of an adaptive filter by compensating for the electro-acoustical path from the output of the processing circuit through the transducer into the at least one microphone, so that the component of the output of the at least one microphone can be corrected to remove components of source audio due to the transducer output. The ANC processing circuit permits the adaptive filter to adapt only when the content of the at least one microphone signal due to the source audio present in the transducer output relative to the microphone signal content due to the ambient audio is greater than a threshold, in order to properly model the acoustic and electrical paths.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

The present invention encompasses noise-canceling techniques and circuits that can be implemented in a personal audio device, such as a wireless telephone. The personal audio device includes an adaptive noise canceling (ANC) circuit that measures the ambient acoustic environment and generates a signal that is injected into the speaker (or other transducer) output to cancel ambient acoustic events. A reference microphone is provided to measure the ambient acoustic environment, and an error microphone is included to measure the ambient audio and transducer output at the transducer, thus giving an indication of the effectiveness of the noise cancelation. A secondary path estimating adaptive filter is used to remove the playback audio from the error microphone signal, in order to generate an error signal. A leakage path estimating adaptive filter is used to remove the playback audio from the reference microphone signal to generate a leakage-corrected reference signal. However, depending on the relative amount of the transducer output relative to the ambient audio present in the error microphone signal, the secondary path estimate and leakage path estimate may not be updated properly. Therefore, update of the secondary path estimate and leakage path estimate is halted or otherwise managed when the relative amount of ambient audio to transducer output source audio content present in the error microphone signal exceeds a threshold.

Figure 1A:
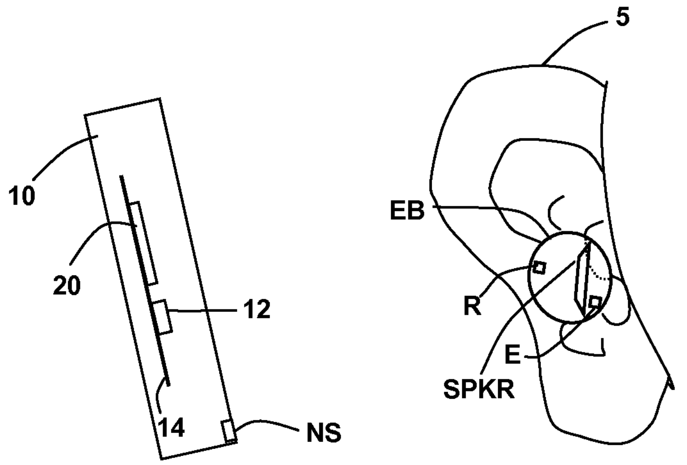
FIG. 1A is an illustration of a wireless telephone 10 coupled to an earbud EB, which is an example of a personal audio device in which the techniques disclosed herein can be implemented.

FIG. 1A shows a wireless telephone 10 proximate to a human ear 5. Illustrated wireless telephone 10 is an example of a device in which the techniques herein may be employed, but it is understood that not all of the elements or configurations illustrated in wireless telephone 10, or in the circuits depicted in subsequent illustrations, are required. Wireless telephone 10 is connected to an earbud EB by a wired or wireless connection, e.g., a BLUETOOTH™ connection (BLUETOOTH is a trademark or Bluetooth SIG, Inc.). Earbud EB has a transducer, such as speaker SPKR, which reproduces source audio including distant speech received from wireless telephone 10, ringtones, stored audio program material, and injection of near-end speech (i.e., the speech of the user of wireless telephone 10). The source audio also includes any other audio that wireless telephone 10 is required to reproduce, such as source audio from web-pages or other network communications received by wireless telephone 10 and audio indications such as battery low and other system event notifications. A reference microphone R is provided on a surface of a housing of earbud EB for measuring the ambient acoustic environment. Another microphone, error microphone E, is provided in order to further improve the ANC operation by providing a measure of the ambient audio combined with the audio reproduced by speaker SPKR close to ear 5, when earbud EB is inserted in the outer portion of ear 5. While the illustrated example shows an earbud implementation of a noise-canceling system, the techniques disclosed herein can also be implemented in a wireless telephone or other personal audio device, in which the output transducer and reference/error microphones are all provided on a housing of the wireless telephone or other personal audio device.

Wireless telephone 10 includes adaptive noise canceling (ANC) circuits and features that inject an anti-noise signal into speaker SPKR to improve intelligibility of the distant speech and other audio reproduced by speaker SPKR. Exemplary circuit 14 within wireless telephone 10 includes an audio CODEC integrated circuit 20 that receives the signals from reference microphone R, near-speech microphone NS, and error microphone E and interfaces with other integrated circuits such as an RF integrated circuit 12 containing the wireless telephone transceiver. In other embodiments of the invention, the circuits and techniques disclosed herein may be incorporated in a single integrated circuit that contains control circuits and other functionality for implementing the entirety of the personal audio device, such as an MP3 player-on-a-chip integrated circuit. Alternatively, the ANC circuits may be included within a housing of earbud EB or in a module located along a wired connection between wireless telephone 10 and earbud EB. For the purposes of illustration, the ANC circuits will be described as provided within wireless telephone 10, but the above variations are understandable by a person of ordinary skill in the art and the consequent signals that are required between earbud EB, wireless telephone 10 and a third module, if required, can be easily determined for those variations. A near-speech microphone NS is provided at a housing of wireless telephone 10 to capture near-end speech, which is transmitted from wireless telephone 10 to the other conversation participant(s). Alternatively, near-speech microphone NS may be provided on the outer surface of a housing of earbud EB, or on a boom (earpiece microphone extension) affixed to earbud EB.

Figure 1B:
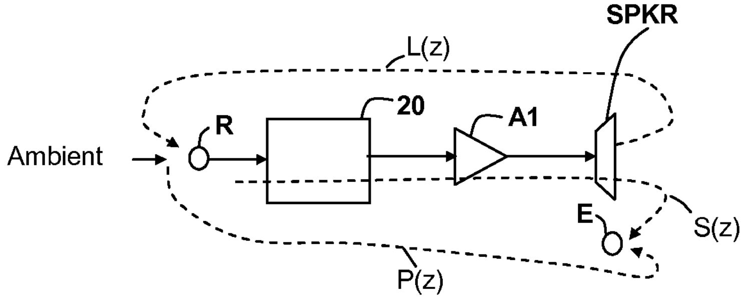
FIG. 1B is an illustration of electrical and acoustical signal paths in FIG. 1A.

FIG. 1B shows a simplified schematic diagram of an audio CODEC integrated circuit 20 that includes ANC processing, as coupled to reference microphone R, which provides a measurement of ambient audio sounds Ambient that is filtered by the ANC processing circuits within audio CODEC integrated circuit 20. Audio CODEC integrated circuit 20 generates an output that is amplified by an amplifier A1 and is provided to speaker SPKR. Audio CODEC integrated circuit 20 receives the signals (wired or wireless depending on the particular configuration) from reference microphone R, near-speech microphone NS and error microphone E and interfaces with other integrated circuits such as an RF integrated circuit 12 containing the wireless telephone transceiver. In other configurations, the circuits and techniques disclosed herein may be incorporated in a single integrated circuit that contains control circuits and other functionality for implementing the entirety of the personal audio device, such as an MP3 player-on-a-chip integrated circuit. Alternatively, multiple integrated circuits may be used, for example, when a wireless connection is provided from earbud EB to wireless telephone 10 and/or when some or all of the ANC processing is performed within earbud EB or a module disposed along a cable connecting wireless telephone 10 to earbud EB.

In general, the ANC techniques illustrated herein measure ambient acoustic events (as opposed to the output of speaker SPKR and/or the near-end speech) impinging on reference microphone R, and also measure the same ambient acoustic events impinging on error microphone E. The ANC processing circuits of illustrated wireless telephone 10 adapt an anti-noise signal generated from the output of reference microphone R to have a characteristic that minimizes the amplitude of the ambient acoustic events at error microphone E. Since acoustic path P(z) extends from reference microphone R to error microphone E, the ANC circuits are essentially estimating acoustic path P(z) combined with removing effects of an electro-acoustic path S(z) that represents the response of the audio output circuits of CODEC IC 20 and the acoustic/electric transfer function of speaker SPKR. The estimated response includes the coupling between speaker SPKR and error microphone E in the particular acoustic environment which is affected by the proximity and structure of ear 5 and other physical objects and human head structures that may be in proximity to earbud EB. Leakage, i.e., acoustic coupling, between speaker SPKR and reference microphone R can cause error in the anti-noise signal generated by the ANC circuits within CODEC IC 20. In particular, desired downlink speech and other internal audio intended for reproduction by speaker SPKR can be partially canceled due to the leakage path L(z) between speaker SPKR and reference microphone R. Since audio measured by reference microphone R is considered to be ambient audio that generally should be canceled, leakage path L(z) represents the portion of the downlink speech and other internal audio that is present in the reference microphone signal and causes the above-described erroneous operation. Therefore, the ANC circuits within CODEC IC 20 include leakage-path modeling circuits that compensate for the presence of leakage path L(z). While the illustrated wireless telephone 10 includes a two microphone ANC system with a third near-speech microphone NS, a system may be constructed that does not include separate error and reference microphones. Alternatively, when near-speech microphone NS is located proximate to speaker SPKR and error microphone E, near-speech microphone NS may be used to perform the function of the reference microphone R. Also, in personal audio devices designed only for audio playback, near-speech microphone NS will generally not be included, and the near-speech signal paths in the circuits described in further detail below can be omitted.

Figure 2:
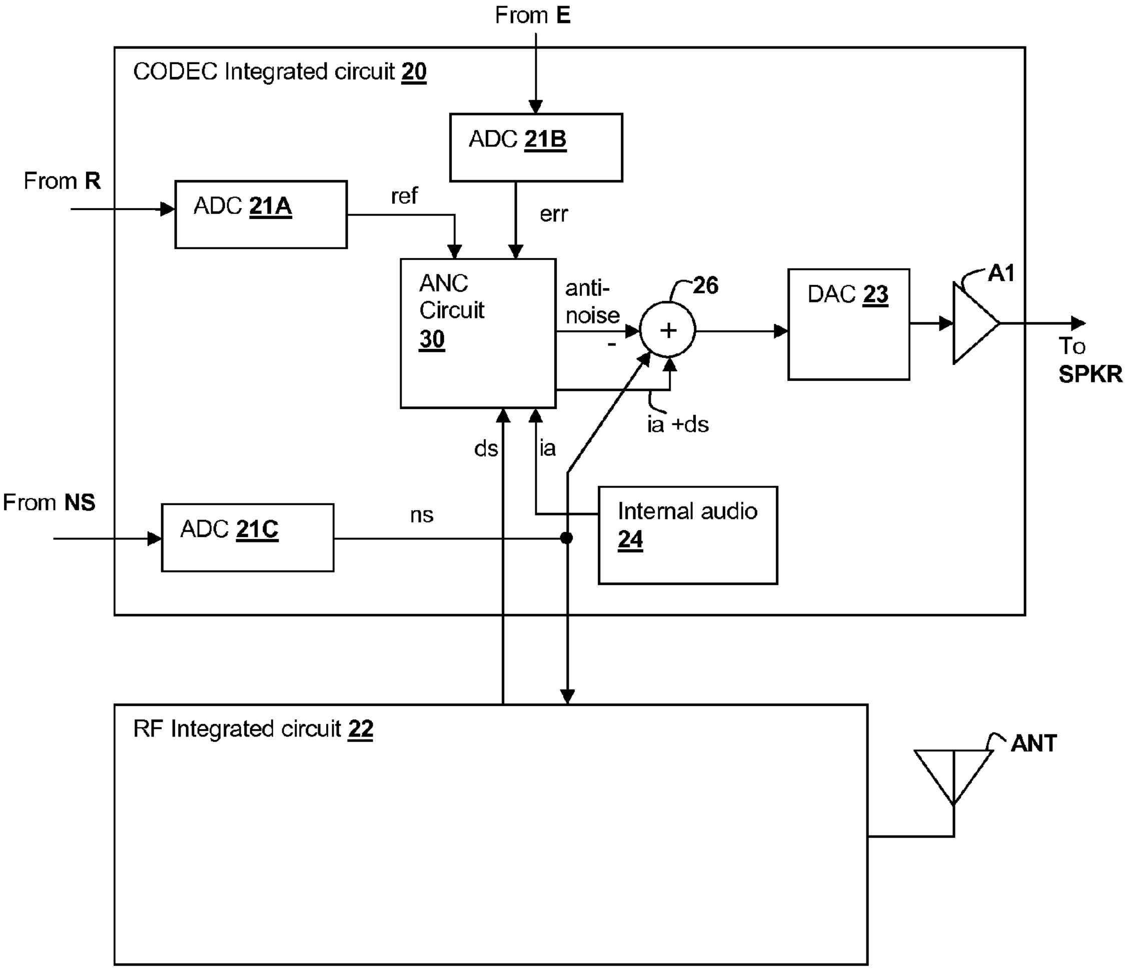
FIG. 2 is a block diagram of circuits within wireless telephone 10.

Referring now to FIG. 2, circuits within wireless telephone 10 are shown in a block diagram. CODEC integrated circuit 20 includes an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near-speech microphone signal and generating a digital representation of near-speech microphone signal ns. CODEC IC 20 generates an output for driving speaker SPKR from an amplifier A1, which amplifies the output of a digital-to-analog converter (DAC) 23 that receives the output of a combiner 26. Combiner 26 combines audio signals is from internal audio sources 24, the anti-noise signal anti-noise generated by ANC circuit 30, which by convention has the same polarity as the noise in reference microphone signal ref and is therefore subtracted by combiner 26, a portion of near-speech signal ns so that the user of wireless telephone 10 hears their own voice in proper relation to downlink speech ds, which is received from radio frequency (RF) integrated circuit 22. In accordance with an embodiment of the present invention, downlink speech ds is provided to ANC circuit 30. Combined downlink speech ds and internal audio is forming source audio (ds+ia) is provided to combiner 26, so that source audio (ds+ia) is always present to estimate acoustic path S(z) with a secondary path adaptive filter within ANC circuit 30. Near-speech signal ns is also provided to RF integrated circuit 22 and is transmitted as uplink speech to the service provider via antenna ANT.

Figure 3:
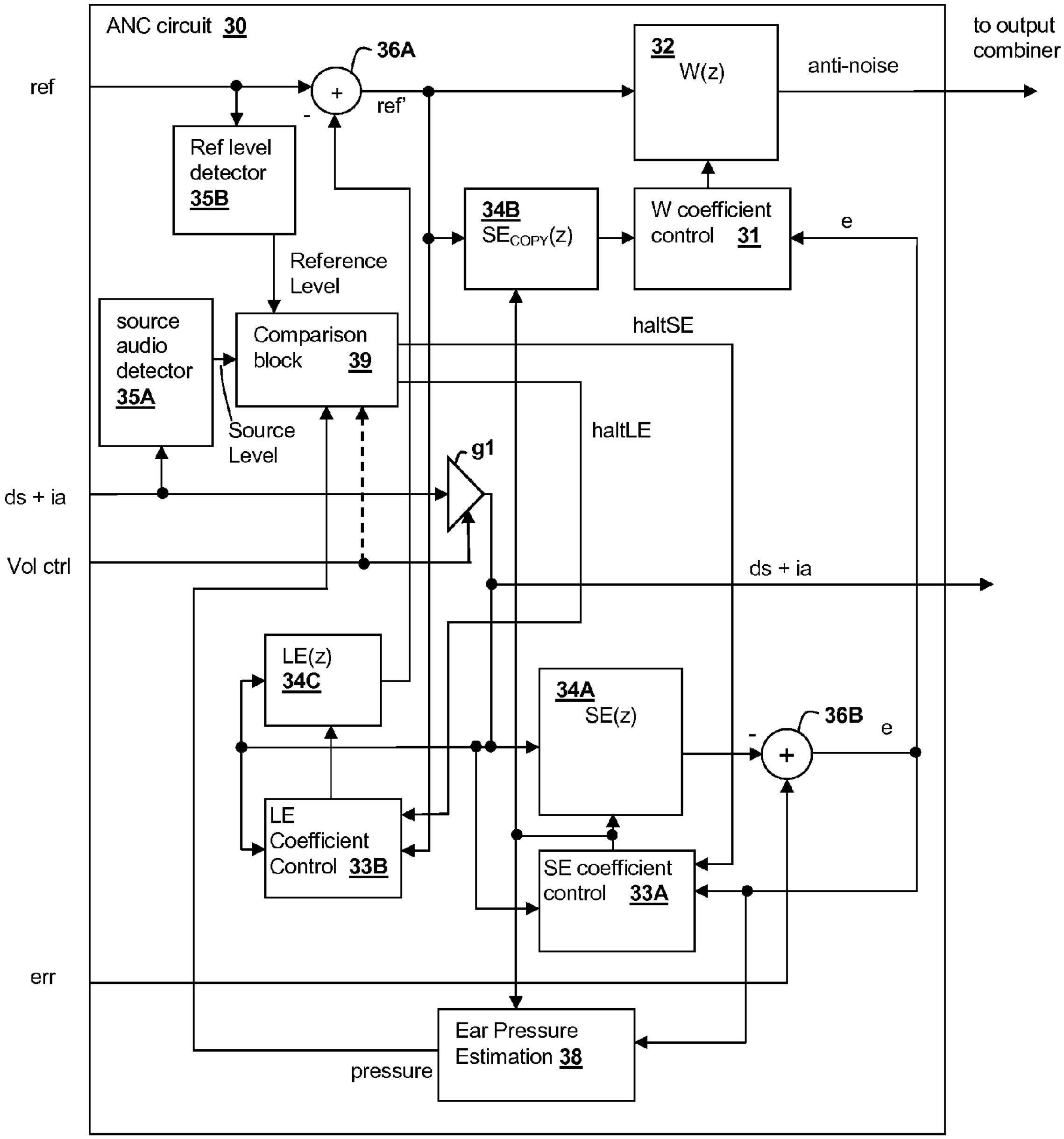
FIG. 3 is a block diagram depicting one example of an implementation of ANC circuit 30 of CODEC integrated circuit 20 of FIG. 2.

FIG. 3 shows one example of details of ANC circuit 30 that can be used to implement ANC circuit 30 of FIG. 2. A combiner 36A removes an estimated leakage signal from reference microphone signal ref, which in the example is provided by a leakage-path adaptive filter 34C having a response LE(z) that models leakage path L(z). Combiner 36A generates a leakage-corrected reference microphone signal ref. An adaptive filter 32 receives leakage-corrected reference microphone signal ref' and under ideal circumstances, adapts its transfer function W(z) to be P(z)/S(z) to generate the anti-noise signal anti-noise, which is provided to an output combiner that combines the anti-noise signal with the audio to be reproduced by speaker SPKR, as exemplified by combiner 26 of FIG. 2. The coefficients of adaptive filter 32 are controlled by a W coefficient control block 31 that uses a correlation of two signals to determine the response of adaptive filter 32, which generally minimizes the error, in a least-mean squares sense, between those components of leakage-corrected reference microphone signal ref' present in error microphone signal err. The signals processed by W coefficient control block 31 are the leakage-corrected reference microphone signal ref' shaped by a copy of an estimate of the response of path S(z) (i.e., response $SE_{COPY}(z)$) provided by filter 34B and another signal that includes error microphone signal err. By transforming leakage-corrected reference microphone signal ref' with a copy of the estimate of the response of path S(z), response $SE_{COPY}(z)$, and minimizing error microphone signal err after removing components of error microphone signal err due to playback of source audio, adaptive filter 32 adapts to the desired response of P(z)/S(z).

In addition to error microphone signal err, the other signal processed along with the output of filter 34B by W coefficient control block 31 includes an inverted amount of the source audio (ds+ia) including downlink audio signal ds and internal audio ia. Source audio (ds+ia) is processed by a filter 34A having response SE(z), of which response $SE_{COPY}(z)$ is a copy. Filter 34B is not an adaptive filter, per se, but has an adjustable response that is tuned to match the response of adaptive filter 34A, so that the response of filter 34B tracks the adapting of adaptive filter 34A. By injecting an inverted amount of source audio (ds+ia) that has been filtered by response SE(z), adaptive filter 32 is prevented from adapting to the relatively large amount of source audio (ds+ia) present in error microphone signal err. By transforming the inverted copy of downlink audio signal ds and internal audio ia with the estimate of the response of path S(z), the source audio (ds+ia) that is removed from error microphone signal err before processing should match the expected version of downlink audio signal ds and internal audio ia reproduced at error microphone signal err. The source audio (ds+ia) matches the amount of source audio (ds+ia) present in error microphone signal err because the electrical and acoustical path of S(z) is the path taken by source audio (ds+ia) to arrive at error microphone E.

To implement the above, adaptive filter 34A has coefficients controlled by SE coefficient control block 33A, which processes the source audio (ds+ia) and error microphone signal err after removal, by a combiner 36B, of the above-described filtered downlink audio signal ds and internal audio ia, that has been filtered by adaptive filter 34A to represent the expected source audio delivered to error microphone E. Adaptive filter 34A is thereby adapted to generate an error signal e from downlink audio signal ds and internal audio ia, that when subtracted from error microphone signal err, contains the content of error microphone signal err that is not due to source audio (ds+ia). Similarly, LE coefficient control 33B also is adapted to minimize the components of source audio (ds+ia) present in leakage-corrected reference microphone signal ref', by adapting to generate an output that represents the source audio (ds+ia) present in reference microphone signal ref. However, if downlink audio signal ds and internal audio ia are both absent or low in amplitude, the content of error microphone signal err and reference microphone signal ref will primarily consist of ambient sounds, which may not be suitable for adapting response SE(z) and response LE(z). Therefore, error microphone signal err may have sufficient amplitude, and yet be unsuitable in content to be useful as a training signal for response SE(z). Similarly, reference microphone signal ref may not contain the proper content to train response LE(z). In ANC circuit 30, a source audio detector 35A detects whether sufficient source audio (ds+ia) is present, and a comparison block 39 updates the secondary path estimate and leakage path estimate if sufficient source audio (ds+ia) is present as indicated by the magnitude of control signal Source Level. The threshold applied to determine whether sufficient source audio (ds+ia) is present can be determined from a magnitude of reference microphone signal ref, as determined by a reference level detector 35B, and as indicated by the magnitude of control signal Reference Level. Comparison block 39 determines whether the magnitude of control signal Source Level is sufficiently great compared to the magnitude of control signal Reference Level and de-asserts control signal haltSE to permit SE coefficient control 33A to update response SE(z) only if sufficient source audio (ds+ia) is present. Similarly, comparison block 39 de-asserts control signal haltLE to permit LE coefficient control 33B to update response LE(z) only if sufficient source audio (ds+ia) is present and may apply the same criteria as for control signal haltSE, or a different threshold may be used. Level detector 35B includes both amplitude detection, and optionally filtering, to obtain the magnitude of reference microphone signal ref. In one exemplary implementation, reference level detector 35B uses a wideband root-mean-square (RMS) detector to determine the magnitude of the ambient sounds. In another example, reference level detector 35B includes a filter that filters reference microphone signal ref to select one or more frequency bands before making an RMS amplitude measurement, so that particular frequencies that will cause improper adaptation of response SE(z) and response LE(z) can be prevented from causing such a disruption, while other sources of ambient noise might be permitted while adapting response SE(z) and response LE(z).

An alternative to using source audio detector 35A to determine the relative amount of source audio (ds+ia) present in error microphone signal err, is to use a volume control signal Vol ctrl as an indication of the magnitude of source audio (ds+ia) being reproduced by speaker SPKR. Volume control signal Vol ctrl is applied to source audio (ds+ia) by a gain stage g1, which also controls the amount of source audio (ds+ia) provided to adaptive filter 34A and adaptive filter 34C. Additionally, whether volume control signal Vol ctrl or control signal Source Level is compared to the threshold provided by control signal Reference Level, the degree of coupling between the listener's ear and personal audio device 10 can be estimated by an ear pressure estimation block 38 to further refine the determination of whether response SE(z) and response LE(z) can be adapted. Ear pressure estimation block 38 generates an indication, control signal pressure, of the degree of coupling between the listener's ear and personal audio device 10. Comparison block 39 can then use control signal Pressure to reduce the threshold provided by control signal Reference Level, since a higher value of control signal Pressure generally indicates that the source audio present in the acoustic output of speaker SPKR is more effectively coupled to the listener's ear, and thus for a given level of source audio (ds+ia), the amount of source audio (ds+ia) heard by the listener is increased with respect to the level of ambient noise. Techniques for determining the degree of coupling between the listener's ear and personal audio device 10 that may be used to implement comparison block 39 are disclosed in U.S. Patent Application Publication US20120207317A1 entitled "EAR-COUPLING DETECTION AND ADJUSTMENT OF ADAPTIVE RESPONSE IN NOISE-CANCELING IN PERSONAL AUDIO DEVICES", the disclosure of which is incorporated herein by reference.

Figure 4:
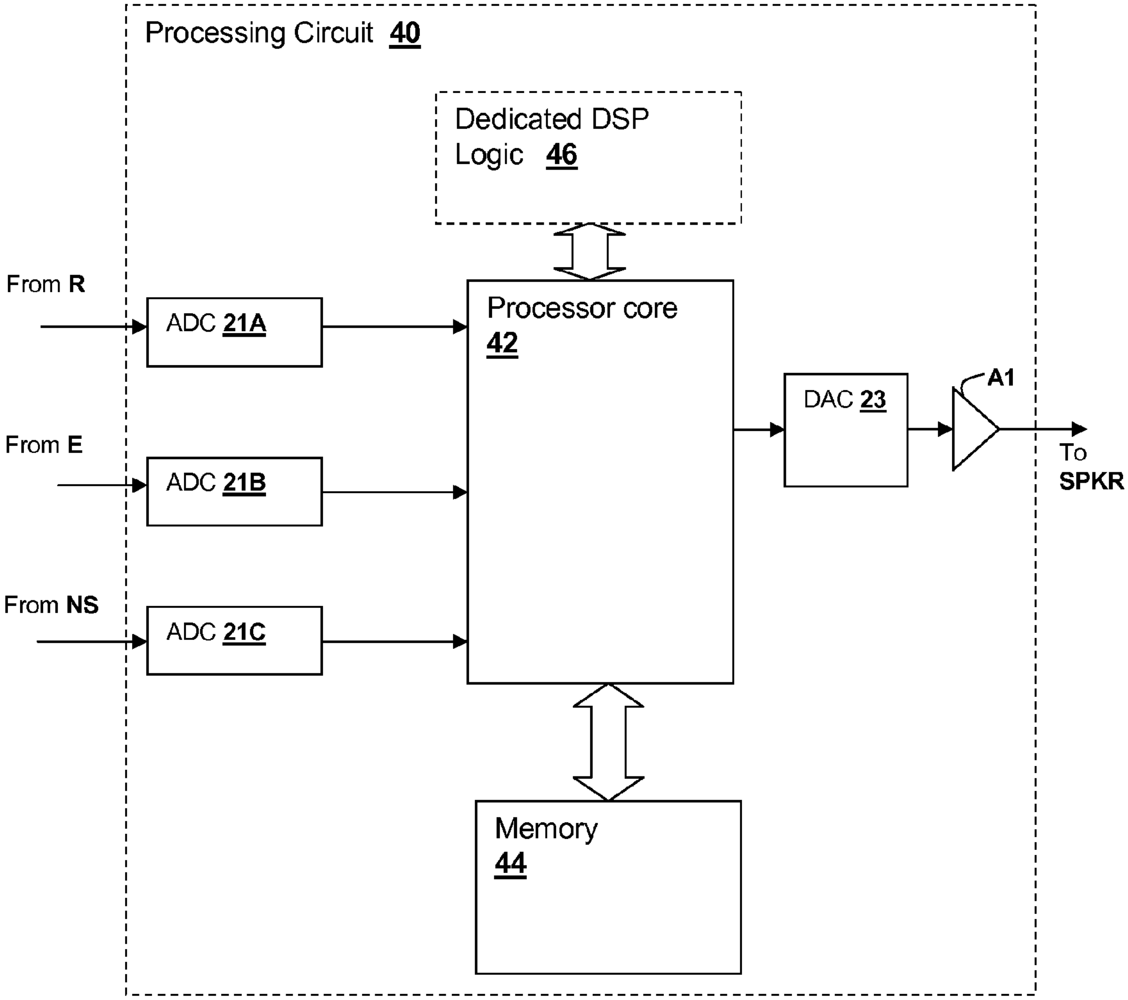
FIG. 4 is a block diagram depicting signal processing circuits and functional blocks within CODEC integrated circuit 20.

Referring now to FIG. 4, a block diagram of an ANC system is shown for implementing ANC techniques as depicted in FIG. 3, and having a processing circuit 40 as may be implemented within CODEC integrated circuit 20 of FIG. 2. Processing circuit 40 includes a processor core 42 coupled to a memory 44 in which program instructions are stored, the program instructions comprising a computer-program product that may implement some or all of the above-described ANC techniques, as well as implementing other signal processing algorithms. Optionally, a dedicated digital signal processing (DSP) logic 46 may be provided to implement a portion of, or alternatively all of, the ANC signal processing provided by processing circuit 40. Processing circuit 40 also includes ADCs 21A-21C, for receiving inputs from reference microphone R, error microphone E and near-speech microphone NS, respectively. DAC 23 and amplifier A1 are also provided by processing circuit 40 for providing the transducer output signal, including anti-noise as described above.

While the invention has been particularly shown and described with reference to the preferred embodiments thereof, it will be understood by those skilled in the art that the foregoing, as well as other changes in form and details may be made therein without departing from the spirit and scope of the invention.

What is claimed is:

1. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

at least one microphone mounted on the housing for providing at least one microphone signal indicative of the ambient audio sounds and that contains a component due to the acoustic output of the transducer; and a processing circuit that generates the anti-noise signal to reduce the presence of the ambient audio sounds heard by the listener, wherein the processing circuit implements an adaptive filter having a response that shapes the source audio and a combiner that removes the source audio from the at least one microphone signal to provide a corrected microphone signal, wherein the processing circuit determines a relative magnitude of a source audio component of the acoustic output of the transducer present in the at least one microphone signal and the ambient audio sounds present in the at least one microphone signal, wherein the processing circuit determines a degree of coupling between the transducer and an ear of the listener and adjusts the determined relative magnitude of the source audio component of the acoustic output of the transducer present in the at least one microphone signal and the ambient audio sounds present in the at least one microphone signal in conformity with the determined degree of coupling, and wherein the processing circuit takes action to prevent improper adaptation of the adaptive filter in response to determining that the relative magnitude of the source audio component of the acoustic output of the transducer present in the at least one microphone signal to the ambient audio sounds present in the at least one microphone signal indicates that the adaptive filter may not adapt properly.

2. The personal audio device of claim 1, wherein the at least one microphone signal includes an error microphone signal provided by an error microphone mounted on the housing proximate to the transducer, wherein the adaptive filter is a secondary path adaptive filter that adapts to model a response of a secondary path taken by the source audio through the transducer and into the error microphone signal , and wherein an output of the secondary path adaptive filter is combined with the error microphone signal to generate an error signal indicative of the source audio component of the acoustic output of the transducer.

3. The personal audio device of claim 2, wherein the at least one microphone signal includes a reference microphone signal provided by a reference microphone mounted on the housing for measuring the ambient audio sounds, and further comprising a leakage path adaptive filter that adapts to model a response of a leakage path taken by the source audio through the transducer and into the reference microphone signal, and wherein an output of the leakage path adaptive filter is combined with the reference microphone signal to generate a leakage-corrected reference microphone signal from which the anti-noise signal is generated.

4. The personal audio device of claim 1, wherein the at least one microphone signal includes a reference microphone signal provided by a reference microphone mounted on the housing for measuring the ambient audio sounds, wherein the adaptive filter is a leakage path adaptive filter that adapts to model a response of a leakage path taken by the source audio through the transducer and into the reference microphone signal, and wherein an output of the leakage path adaptive filter is combined with the reference microphone signal to generate a leakage-corrected reference microphone signal from which the anti-noise signal is generated.

5. The personal audio device of claim 2, wherein the processing circuit computes a ratio of a first magnitude of the source audio component of the acoustic output of the transducer present in the error signal relative to a second magnitude of the ambient audio sounds present in the error signal and compares the ratio to a threshold, wherein the processing circuit further halts adaptation of the secondary path adaptive filter in response to determining that the ratio is less than the threshold.

6. The personal audio device of claim 1, wherein the processing circuit detects a magnitude of the source audio and uses the magnitude of the source audio to determine the magnitude of the source audio component of the acoustic output of the transducer present in the at least one microphone signal.

7. The personal audio device of claim 1, wherein the processing circuit uses a volume control setting applied as gain to the source audio to determine the magnitude of the source audio component of the acoustic output of the transducer present in the at least one microphone signal.

8. The personal audio device of claim 1, wherein the processing circuit detects a magnitude of the ambient sounds using the at least one microphone, and wherein the processing circuit uses the magnitude of the ambient audio sounds to determine the magnitude of the ambient audio sounds present in the at least one microphone signal.

9. The personal audio device of claim 8, wherein the processing circuit detects the magnitude of the ambient sounds by determining a wideband root-mean-square amplitude of at least one microphone signal generated by the at least one microphone.

10. The personal audio device of claim 8, wherein the processing circuit detects the magnitude of the ambient sounds by determining a root-mean-square amplitude of at least one microphone signal generated by the at least one microphone in one or more predetermined frequency bands.

11. The personal audio device of claim 8, wherein the processing circuit detects a magnitude of the source audio and compares the magnitude of the source audio to a magnitude of at least one microphone signal generated by the at least one microphone to determine the relative magnitude of the source audio component of the acoustic output of the transducer present in the at least one microphone signal and the ambient audio sounds present in the at least one microphone signal.

12. The personal audio device of claim 11, wherein the processing circuit adjusts the comparing of the magnitude of the source audio to the magnitude of the at least one microphone signal by adjusting the magnitude of the at least one microphone signal that is compared to the magnitude of the at least one microphone signal in conformity with the determined degree of coupling.

13. A method of countering effects of ambient audio sounds by a personal audio device, the method comprising:

adaptively generating an anti-noise signal to reduce the presence of the ambient audio sounds heard by the listener;

combining the anti-noise signal with source audio;

providing a result of the combining to a transducer;

measuring the ambient audio sounds and an acoustic output of the transducer with at least one microphone;

implementing an adaptive filter having a response that shapes the source audio and a combiner that removes the source audio from at least one microphone signal to provide a corrected microphone signal to the at least one microphone;

determining a relative magnitude of a source audio component of the acoustic output of the transducer present in the at least one microphone signal and the ambient audio sounds present in the at least one microphone signal;

determining a degree of coupling between the transducer and an ear of the listener and adjusting the determined relative magnitude of the source audio component of the acoustic output of the transducer present in the at least one microphone signal and the ambient audio sounds present in the at least one microphone signal in conformity with the determined degree of coupling; and taking action to prevent improper adaptation of the adaptive filter in response to determining that the relative magnitude of the source audio component of the acoustic output of the transducer present in the at least one microphone signal to the ambient audio sounds present in the at least one microphone signal indicates that the adaptive filter may not adapt properly.

14. The method of claim 13, wherein the at least one microphone signal includes an error microphone signal provided by an error microphone mounted on the housing proximate to the transducer, wherein the adaptive filter is a secondary path adaptive filter that adapts to model a response of a secondary path taken by the source audio through the transducer and into the error microphone signal, and wherein the method further comprises combining an output of the secondary path adaptive filter with the error microphone signal to generate an error signal indicative of the source audio component of the acoustic output of the transducer.

15. The method of claim 14, wherein the at least one microphone signal further includes a reference microphone signal provided by a reference microphone mounted on the housing for measuring the ambient audio sounds, and wherein the method further comprising:

generating a leakage correction signal using a leakage path adaptive filter that adapts to model a response of a leakage path taken by the source audio through the transducer and into the reference microphone signal; and combining the leakage correction signal with the reference microphone signal to generate a reference signal from which the anti-noise signal is generated.

16. The method of claim 13, wherein the at least one microphone signal includes a reference microphone signal provided by a reference microphone mounted on the housing for measuring the ambient audio sounds, and wherein the method further comprising:

generating a leakage correction signal using a leakage path adaptive filter that adapts to model a response of a leakage path taken by the source audio through the transducer and into the reference microphone signal; and combining the leakage correction signal with the reference microphone signal to generate a reference signal from which the anti-noise signal is generated.

17. The method of claim 14, wherein the determining comprises computing a ratio of a first magnitude of the source audio component of the acoustic output of the transducer present in the error signal relative to a second magnitude of the ambient audio sounds present in the error signal and comparing the ratio to a threshold, and wherein the taking action comprises halting adaptation of the secondary path adaptive filter in response to determining that the ratio is less than the threshold.

18. The method of claim 13, further comprising detecting a magnitude of the source audio, wherein the determining uses the detected magnitude of the source audio to determine the magnitude of the source audio component of acoustic output of the transducer present in the at least one microphone signal.

19. The method of claim 13, wherein the determining uses a volume control setting applied as gain to the source audio to determine the magnitude of the source audio component of the acoustic output of the transducer present in the at least one microphone signal.

20. The method of claim 13, further comprising detecting a magnitude of the ambient sounds using the at least one microphone, and wherein the determining uses the magnitude of the ambient audio sounds to determine the magnitude of the ambient audio sounds present in the at least one microphone signal.

21. The method of claim 20, wherein the detecting detects the magnitude of the ambient sounds by determining a wide-band root-mean-square amplitude of at least one microphone signal generated by the at least one microphone.

22. The method of claim 20, wherein the detecting detects the magnitude of the ambient sounds by determining a root-mean-square amplitude of at least one microphone signal generated by the at least one microphone in one or more predetermined frequency bands.

23. The method of claim 20, wherein the detecting detects a magnitude of the source audio and compares the magnitude of the source audio to a magnitude of at least one microphone signal generated by the at least one microphone to determine the relative magnitude of the source audio component of the acoustic output of the transducer present in the at least one microphone signal and the ambient audio sounds present in the at least one microphone signal.

24. The method of claim 23, further comprising adjusting the comparing of the magnitude of the source audio to a magnitude of the at least one microphone signal by adjusting the magnitude of the at least one microphone signal that is compared to the magnitude of the at least one microphone signal in conformity with the determined degree of coupling.

25. An integrated circuit for implementing at least a portion of a personal audio device, comprising:

an output for providing an output signal to an output transducer including both source audio for playback to a listener and an anti-noise signal for countering the effects of ambient audio sounds in an acoustic output of the transducer;

at least one microphone input for receiving at least one microphone signal indicative of the ambient audio sounds and that contains a component due to the acoustic output of the transducer; and a processing circuit that adaptively generates the anti-noise signal to reduce the presence of the ambient audio sounds heard by the listener, wherein the processing circuit implements an adaptive filter having a response that shapes the source audio and a combiner that removes the source audio from the at least one microphone signal to provide a corrected microphone signal, wherein the processing circuit determines a relative magnitude of a source audio component of the acoustic output of the transducer present in the at least one microphone signal and the ambient audio sounds present in the at least one microphone signal, wherein the processing circuit determines a degree of coupling between the transducer and an ear of the listener and adjusts the determined relative magnitude of the source audio component of the acoustic output of the transducer present in the at least one microphone signal and the ambient audio sounds present in the at least one microphone signal in conformity with the determined degree of coupling, and wherein the processing circuit takes action to prevent improper adaptation of the adaptive filter in response to determining that the relative magnitude of the source audio component of the acoustic output of the transducer present in the at least one microphone signal to the ambient audio sounds present in the at least one microphone signal indicates that the adaptive filter may not adapt properly.

26. The integrated circuit of claim 25, wherein the at least one microphone signal includes an error microphone signal indicative of the ambient audio sounds and the acoustic output of the transducer, wherein the adaptive filter is a secondary path adaptive filter that adapts to model a response of a secondary path taken by the source audio through the transducer and into the error microphone signal, and wherein an output of the secondary path adaptive filter is combined with the error microphone signal to generate an error signal indicative of the source audio component of the acoustic output of the transducer.

27. The integrated circuit of claim 26, wherein the at least one microphone signal includes a reference microphone signal indicative of the ambient audio sounds, and further comprising a leakage path adaptive filter that adapts to model a response of a leakage path taken by the source audio through the transducer and into the reference microphone signal, and wherein an output of the leakage path adaptive filter is combined with the reference microphone signal to generate a leakage-corrected reference microphone signal from which the anti-noise signal is generated.

28. The integrated circuit of claim 25, wherein the at least one microphone signal includes a reference microphone signal indicative of the ambient audio sounds, wherein the adaptive filter is a leakage path adaptive filter that adapts to model a response of a leakage path taken by the source audio through the transducer and into the reference microphone signal, and wherein an output of the leakage path adaptive filter is combined with the reference microphone signal to generate a reference signal from which the anti-noise signal is generated.

29. The integrated circuit of claim 26, wherein the processing circuit computes a ratio of a first magnitude of the source audio component of the acoustic output of the transducer present in the error signal relative to a second magnitude of the ambient audio sounds present in the error signal and compares the ratio to a threshold, wherein the processing circuit further halts adaptation of the secondary path adaptive filter in response to determining that the ratio is less than the threshold.

30. The integrated circuit of claim 25, wherein the processing circuit detects a magnitude of the source audio and uses the magnitude of the source audio to determine the magnitude of the source audio component of the acoustic output of the transducer present in the at least one microphone signal.

31. The integrated circuit of claim 25, wherein the processing circuit uses a volume control setting applied as gain to the source audio to determine the magnitude of the source audio component of the acoustic output of the transducer present in the at least one microphone signal.

32. The integrated circuit of claim 25, wherein the processing circuit detects a magnitude of the ambient sounds using the at least one microphone, and wherein the processing circuit uses the magnitude of the ambient audio sounds to determine the magnitude of the ambient audio sounds present in the at least one microphone signal.

33. The integrated circuit of claim 32, wherein the processing circuit detects the magnitude of the ambient sounds by determining a wideband root-mean-square amplitude of the at least one microphone signal.

34. The integrated circuit of claim 32, wherein the processing circuit detects the magnitude of the ambient sounds by determining a root-mean-square amplitude of the at least one microphone signal in one or more predetermined frequency bands.

35. The integrated circuit of claim 32, wherein the processing circuit detects a magnitude of the source audio and compares the magnitude of the source audio to a magnitude of the at least one microphone signal to determine the relative magnitude of the source audio component of the acoustic output of the transducer present in the at least one microphone signal and the ambient audio sounds present in the at least one microphone signal.

36. The integrated circuit of claim 35, wherein the processing circuit adjusts the comparing of the magnitude of the source audio to the magnitude of the at least one microphone signal by adjusting the magnitude of the at least one microphone signal that is compared to the magnitude of the at least one microphone signal in conformity with the determined degree of coupling.

* * * * *